United States Patent [19]

de la Mettrie et al.

[11] Patent Number: 5,989,295
[45] Date of Patent: Nov. 23, 1999

[54] OXIDATION DYE COMPOSITION FOR KERATIN FIBRES, COMPRISING AN ANIONIC AMPHIPHILIC POLYMER

[75] Inventors: Roland de la Mettrie, Le Vesinet; Françoise Boudy, Paris, both of France

[73] Assignee: L'Oréal, Paris, France

[21] Appl. No.: 08/923,969

[22] Filed: Sep. 5, 1997

[30] Foreign Application Priority Data

Sep. 6, 1996 [FR] France .................................. 96 10921

[51] Int. Cl.⁶ ....................................................... A61K 7/13
[52] U.S. Cl. ..................... 8/406; 8/407; 8/408; 8/409; 8/410; 8/411; 8/412; 8/554; 8/557; 8/558
[58] Field of Search .............................. 8/405, 406, 407, 8/408, 409, 410, 411, 412, 435, 554, 557, 558

[56] References Cited

U.S. PATENT DOCUMENTS

| | | | |
|---|---|---|---|
| 3,200,040 | 8/1965 | Fritz-Walter Lange et al. | 546/264 |
| 3,530,215 | 9/1970 | Grief et al. | 424/70.16 |
| 3,915,921 | 10/1975 | Schaltzer, Jr. | 526/238.23 |
| 3,973,901 | 8/1976 | Micchelli et al. | 8/425 |
| 3,990,991 | 11/1976 | Gerstein | 510/124 |
| 4,003,699 | 1/1977 | Rose et al. | 8/409 |
| 4,217,914 | 8/1980 | Jacquet et al. | 132/7 |
| 4,240,450 | 12/1980 | Grollier et al. | 132/7 |
| 4,283,384 | 8/1981 | Jacquet et al. | 8/405 |
| 4,445,521 | 5/1984 | Grollier et al. | 132/7 |
| 4,509,949 | 4/1985 | Huang et al. | 8/558 |
| 4,526,781 | 7/1985 | Goldberg et al. | 424/70 |
| 4,530,830 | 7/1985 | McKaba et al. | 424/71 |
| 4,567,038 | 1/1986 | Ciaudelli et al. | 424/59 |
| 4,567,039 | 1/1986 | Stadnick et al. | 132/70 |
| 4,714,610 | 12/1987 | Gerstein | 424/70 |
| 4,776,855 | 10/1988 | Pohl et al. | 8/406 |
| 4,839,166 | 6/1989 | Grollier et al. | 424/71 |
| 4,973,475 | 11/1990 | Schnetzinger et al. | 424/70 |
| 4,986,983 | 1/1991 | Gerstein | 424/70 |
| 5,061,289 | 10/1991 | Clausen et al. | 8/405 |
| 5,071,441 | 12/1991 | Schnetzinger et al. | 8/405 |
| 5,163,010 | 11/1992 | Klein et al. | 364/479 |
| 5,290,555 | 3/1994 | Guthauser et al. | 424/401 |
| 5,304,370 | 4/1994 | Hawkins et al. | 424/71 |
| 5,306,489 | 4/1994 | Goldberg et al. | 424/71 |
| 5,374,420 | 12/1994 | Gerstein | 424/70.11 |
| 5,376,146 | 12/1994 | Casperson et al. | 8/408 |
| 5,380,340 | 1/1995 | Neunhoeffer et al. | 8/409 |
| 5,389,363 | 2/1995 | Snyder et al. | 424/70.7 |
| 5,391,368 | 2/1995 | Gerstein | 424/70.13 |
| 5,393,305 | 2/1995 | Cohen et al. | 8/406 |
| 5,443,855 | 8/1995 | Tietjen et al. | 424/401 |
| 5,519,063 | 5/1996 | Mondet et al. | 514/772.4 |
| 5,534,267 | 7/1996 | Neunhoeffer et al. | 424/701 |
| 5,645,609 | 6/1997 | Andrean et al. | 8/405 |
| 5,663,366 | 9/1997 | Neunhoeffer et al. | 548/371.4 |
| 5,700,456 | 12/1997 | Dubief et al. | 424/70.17 |

FOREIGN PATENT DOCUMENTS

| | | |
|---|---|---|
| 133905 | 3/1985 | European Pat. Off. . |
| 167866 | 1/1986 | European Pat. Off. . |
| 168719 | 1/1986 | European Pat. Off. . |
| 0 216 479 | 4/1987 | European Pat. Off. . |
| 533408 | 3/1993 | European Pat. Off. . |
| 0 673 641 | 9/1995 | European Pat. Off. . |
| 0769290 | 4/1997 | European Pat. Off. . |
| 2 327 761 | 5/1977 | France . |
| 2 446 633 | 1/1979 | France . |
| 2 679 444 | 1/1993 | France . |
| 1026978 | 4/1966 | United Kingdom . |
| 1066207 | 4/1967 | United Kingdom . |
| 1153196 | 5/1969 | United Kingdom . |
| 1236560 | 6/1971 | United Kingdom . |
| 1257907 | 12/1971 | United Kingdom . |
| 1 541 670 | 3/1979 | United Kingdom . |
| 2 124 081 | 2/1994 | United Kingdom . |
| 91 15186 | 10/1991 | WIPO . |
| 91 15187 | 10/1991 | WIPO . |
| WO 94/04125 | 3/1994 | WIPO . |

OTHER PUBLICATIONS

File History for U.S. Patent No. 4,776,855, Pohl et al, Oct. 1988.
International Cosmetic Ingredient Dictionary, Fifth Edition, vol. 1, p. 14, No month available 1993.
International Cosmetic Ingredient Dictionary, Fifth Edition, vol. 2, p. 1040, No month available 1993.
Results from Dialog Search performed by Assignee, 83 pages, Mar. 1997.
Results from Dialog Search performed by Assignee, 19 pages, Mar. 1997.
English Language Abstract of JP 88–169571, Jul. 1988.
English Language Abstract of JP 91–333495, Dec. 1991.

Primary Examiner—Caroline D. Liott
Attorney, Agent, or Firm—Finnegan, Henderson, Farabow, Garrett & Dunner, L.L.P.

[57] ABSTRACT

An oxidation dye composition for keratin fibers, in particular for human keratin fibers such as the hair, comprising, in a medium which is suitable for dyeing, at least one oxidation dye precursor and optionally one or more couplers, which is characterized in that it also contains an anionic amphiphilic polymer containing at least one hydrophilic unit of an unsaturated olefinic carboxylic acid, and at least one hydrophobic unit which is a ($C_{10}$–$C_{30}$)alkyl ester of unsaturated carboxylic acid, preferably exclusively of said ($C_{10}$–$C_{30}$) alkyl ester of unsaturated carboxylic acid. The oxidation dye compositions are used in dyeing processes and dyeing devices.

59 Claims, No Drawings

OXIDATION DYE COMPOSITION FOR KERATIN FIBRES, COMPRISING AN ANIONIC AMPHIPHILIC POLYMER

The present invention relates to a composition for the oxidation dyeing of keratin fibres, and in particular human keratin fibres such as the hair, this composition comprising at least one oxidation dye precursor and optionally one or more couplers and at least one anionic amphiphilic polymer containing at least one hydrophilic unit of an unsaturated olefinic carboxylic acid, and at least one hydrophobic unit of a ($C_{10}$–$C_{30}$)alkyl ester of unsaturated carboxylic acid, preferably exclusively of said ($C_{10}$–$C_{30}$)alkyl ester of unsaturated carboxylic acid.

It is known to dye keratin fibres, and in particular human hair, with dye compositions containing oxidation dye precursors, which are generally known as "oxidation bases", in particular ortho- or para-phenylenediamines, ortho- or para-aminophenols and heterocyclic bases.

Oxidation dye precursors are initially colourless or weakly coloured compounds which develop their dyeing power on the hair in the presence of oxidizing agents, leading to the formation of coloured compounds. The formation of these coloured compounds results either from an oxidative condensation of the oxidation bases with themselves or from an oxidative condensation of the oxidation bases with colour modifier compounds, or "couplers", which are generally present in the dye compositions used in oxidation dyeing and are represented more particularly by meta-phenylenediamines, meta-aminophenols and meta-diphenols, and certain heterocyclic compounds.

The variety of molecules used, which comprise, on the one hand, the oxidation bases, and, on the other hand, the couplers, makes it possible to obtain a very wide range of colours.

In order to localize the oxidation dye product to application on the hair, in order for it not to run down the face or beyond the areas which it is proposed to dye, use has been made hitherto of traditional thickeners such as crosslinked polyacrylic acid, hydroxyethylcelluloses, waxes or alternatively mixtures of nonionic surfactants with an HLB (hydrophilic-lipophilic balance) which, when suitably selected, give rise to the gelling effect when they are diluted with water and/or surfactants.

However, the inventors have observed that the ingredients of the traditional thickener, surfactant and solvent type generally impede the rise of the dye on the fibres, which is reflected in a dull shade and also in the use of a larger amount of dye, solvent and/or surfactants in order to dissolve the dye, if it is nevertheless required to obtain an intense shade.

Moreover, the inventors have also observed that after mixing with the oxidizing agent, the dye compositions containing the oxidation dye precursor(s) and optionally the coupler(s), and also the said ingredients, lost some of their gelled nature and consequently gave rise to undesirable running.

Now, after considerable research conducted in this matter, the inventors have discovered that it is possible to obtain oxidation dye compositions (after mixing with the oxidizing agent) which do not run and thus remain better localized at the point of application, and which also make it possible to obtain more chromatic (more luminous) and more intense shades if an effective amount of an anionic amphiphilic polymer containing at least one hydrophilic unit of unsaturated olefinic carboxylic acid type, and at least one hydrophobic unit which is of ($C_{10}$–$C_{30}$) alkyl ester of unsaturated carboxylic acid type, preferably exclusively of said ($C_{10}$–$C_{30}$)alkyl ester of unsaturated carboxylic acid type, is introduced (i) either into the composition containing the oxidation dye precursor(s) and optionally the coupler(s) (or composition (A)), or (ii) into the oxidizing composition (or composition (B)), or (iii) into the two compositions at once.

For the purposes of the present invention, the chromaticity (luminosity) is defined by the value $c^*$ in the $L^*$, $a^*$, $b^*$ colorimetric notation system of the Commission Internationale de l'Eclairage (C.I.E.) (International Commission on Light). This value is equal to the square root of the sum $a^2+b^2$ (+a is red, –a is green, +b is yellow, –b is blue). The shade is proportionately more luminous the larger the value of $c^*$. In this notation system, $L^*$ defines the intensity of the shade. The shade is proportionately more intense the lower the value of $L^*$ (0=black, 100=white).

These discoveries form the basis of the present invention.

The subject of the present invention is thus an oxidation dye composition for keratin fibres, in particular for human keratin fibres such as the hair, of the type comprising, in a medium which is suitable for dyeing, at least one oxidation dye precursor (oxidation base) and, where appropriate, one or more couplers, which is characterized in that it also contains at least one anionic amphiphilic polymer containing at least one hydrophilic unit of an unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid.

By means of the present invention, it is also, and advantageously, possible to reduce the consumption of surfactants, or even to dispense with them altogether.

The invention also makes it possible to reduce the amount of active dyestuffs used in the dye compositions, when compared with the standard and known techniques of the prior art.

Another subject of the present invention relates to a ready-to-use composition for dyeing keratin fibres, which contains at least one oxidation dye precursor and optionally at least one coupler, and at least one anionic amphiphilic polymer containing at least one hydrophilic unit of an unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid, and an oxidizing agent.

The invention is also directed towards a process for dyeing keratin fibres, and in particular human keratin fibres such as the hair, comprising the steps of applying to these fibres at least one composition (A1) containing, in a medium which is suitable for dyeing, at least one oxidation dye precursor and optionally at least one coupler, in combination with at least one anionic amphiphilic polymer containing at least one hydrophilic unit of unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid, and of developing the colour at alkaline, neutral or acidic pH using an oxidizing agent which is mixed, only at the time of use, with the composition (A1) or which is present in a composition (B1) that is applied sequentially without intermediate rinsing.

The invention is also directed towards a variant of this process, which comprises the steps of applying to the fibres at least one composition (A2) containing, in a medium which is suitable for dyeing, at least one oxidation dye precursor and optionally at least one coupler, this being in the presence or absence of anionic amphiphilic polymer containing at least one hydrophilic unit of unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid, and of developing the colour at alkaline, neutral or acidic pH using an oxidizing composition (B2) which contains an oxidizing agent and an effective amount of at least one anionic amphiphilic polymer containing at least one hydrophilic unit of an unsaturated olefinic carboxylic acid, and at least one hydrophobic unit which is a ($C_{10}$–$C_{30}$) alkyl ester of unsaturated carboxylic acid type, preferably exclusively of said ($C_{10}$–$C_{30}$)alkyl ester of unsaturated carboxylic acid, and which is mixed, only at the time of use, with the composition (A2) or which is applied sequentially without intermediate rinsing.

The subject of the invention is also multi-compartment "kits" or devices for dyeing, the first compartment of which contains at least one oxidation dye precursor, optionally at least one coupler, and at least one anionic amphiphilic polymer containing at least one hydrophilic unit of unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid, and the second compartment of which contains an oxidizing agent.

According to another variant, the subject of the invention is also multi-compartment "kits" or devices for dyeing, the first compartment of which contains at least one oxidation dye precursor, optionally at least one coupler, this being in the presence or absence of anionic amphiphilic polymer containing at least one hydrophilic unit of unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid, and the second compartment of which contains an oxidizing agent and an effective amount of at least one anionic amphiphilic polymer containing at least one hydrophilic unit of unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid.

The invention also relates to the use of the oxidation dye composition defined above or of a multi-compartment "kit" or device for dyeing as defined above for the dyeing of human keratin fibres such as the hair.

However, other characteristics, aspects, objects and advantages of the invention will become even more apparent on reading the description and the examples which follow.

The anionic amphiphilic polymers containing at least one hydrophilic unit of unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid, which are used according to the invention, are preferably chosen from those whose hydrophilic unit of unsaturated olefinic carboxylic acid corresponds to the monomer of formula (I) below:

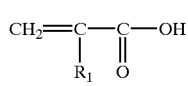

(I)

in which formula $R_1$ denotes H or $CH_3$ or $C_2H_5$, that is to say acrylic acid, methacrylic acid or ethacrylic acid units, and in which the hydrophobic unit of ($C_{10}$–$C_{30}$) alkyl ester of unsaturated carboxylic acid corresponds to the monomer of formula (II) below:

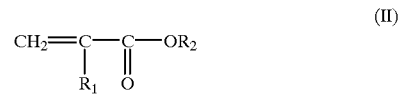

(II)

in which formula $R_1$ denotes H or $CH_3$ or $C_2H_5$ (that is to say acrylate, methacrylate or ethacrylate units) and preferably H (acrylate units) or $CH_3$ (methacrylate units), $R_2$ denoting a $C_{10}$–$C_{30}$, and preferably $C_{12}$–$C_{22}$, alkyl radical.

($C_{10}$–$C_{30}$) alkyl esters of unsaturated carboxylic acids in accordance with the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are described and prepared, for example, according to U.S. Pat. Nos. 3,915,921 and 4,509,949, the disclosures of which are specifically incorporated by reference herein.

The anionic amphiphilic polymers which may be used in the context of the present invention may more particularly denote polymers formed from a mixture of monomers comprising:

(i) essentially acrylic acid, an ester of formula (II) below:

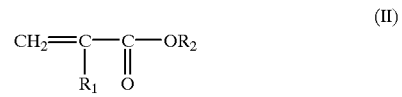

(II)

in which $R_1$ denotes H or $CH_3$, $R_2$ denoting an alkyl radical having from 12 to 22 carbon atoms, and a crosslinking agent, such as, for example, those comprising 95 to 60% by weight of acrylic acid (hydrophilic unit), 4 to 40% by weight of $C_{10}$–$C_{30}$ alkyl acrylate (hydrophobic unit) and 0 to 6% by weight of polymerizable crosslinking monomer, or 98 to 96% by weight of acrylic acid (hydrophilic unit), 1 to 4% by weight of $C_{10}$–$C_{30}$ alkyl acrylate (hydrophobic unit) and 0.1 to 0.6% by weight of polymerizable crosslinking monomer, (ii) essentially acrylic acid and lauryl methacrylate, such as that formed from 66% by weight of acrylic acid and 34% by weight of lauryl methacrylate.

The said crosslinking agent is a monomer containing a group

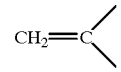

with at least one other polymerizable group whose unsaturated bonds are not conjugated to each other. Mention may be made in particular of polyallyl ethers such as, in particular, polyallyl sucrose and polyallyl pentaerythritol.

Among the above said polymers, the products sold by the company Goodrich under the tradenames Pemulen TR1, Pemulen TR2, Carbopol 1382, and, even more preferably, Pemulen TR1, and the product sold by the company SEPC under the name Coatex SX, are most particularly preferred according to the present invention.

The anionic amphiphilic polymers containing at least one hydrophilic unit of unsaturated olefinic carboxylic acid, and at least one hydrophobic unit which is a ($C_{10}$–$C_{30}$) alkyl ester of unsaturated carboxylic acid, preferably exclusively said ($C_{10}$–$C_{30}$)alkyl ester of unsaturated carboxylic acid, are preferably used according to the invention in an amount which may range from about 0.05 to 10% by weight relative to the total weight of the dye composition applied to the fibres. More preferably, this amount ranges from about 0.2 to 5% by weight.

The oxidation dye precursors which may be used in the context of the present invention are chosen from those known conventionally in oxidation dyeing, and among which mention may be made in particular of:

the para-phenylenediamines of formula (III) below, and the addition salts thereof with an acid:

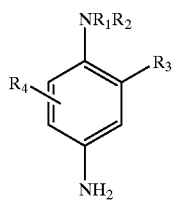

(III)

in which:
$R_1$ represents a hydrogen atom or a $C_1$–$C_4$ alkyl, $C_1$–$C_4$ monohydroxyalkyl, $C_2$–$C_4$ polyhydroxyalkyl or 4'-aminophenyl radical,
$R_2$ represents a hydrogen atom or a $C_1$–$C_4$ alkyl, $C_1$–$C_4$ monohydroxyalkyl or $C_2$–$C_4$ polyhydroxyalkyl radical,
$R_3$ represents a hydrogen atom, a halogen atom such as a chlorine atom, or a $C_1$–$C_4$ alkyl, sulpho, carboxyl, $C_1$–$C_4$ monohydroxyalkyl or $C_1$–$C_4$ hydroxyalkoxy radical, and
$R_4$ represents a hydrogen atom or a $C_1$–$C_4$ alkyl radical.

Among the para-phenylenediamines of formula (III) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxy-ethyl-para-phenylenediamine, 2-fluoro-para-phenylene-diamine, 2-isopropyl-para-phenylenediamine, N-(β-hydroxy-propyl)-para-phenylenediamine, 2-hydroxy-methyl-para-phenylenediamine, N,N-dimethyl-3-methyl-para-phenylenediamine, N-ethyl-N(β-hydroxyethyl)-para-phenylenediamine, N-(β,γ-dihydroxypropyl)para-phenylenediamine, N-(4'-aminophenyl)-para-phenylene-diamine, N-phenyl-para-phenylenediamine and 2-β-hydroxy-ethyloxy-para-phenylenediamine, and the addition salts thereof with an acid.

Among the para-phenylenediamines of formula (III) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylene-diamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid, are most particularly preferred.

the bis(phenyl)alkylenediamines corresponding to formula (IV) below, and the addition salts thereof with an acid:

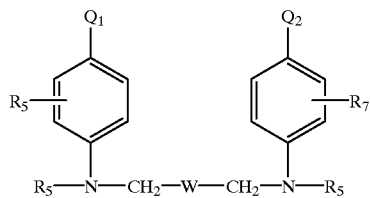

(IV)

in which:
$Q_1$ and $Q_2$, which may be identical or different, represent a hydroxyl radical or a radical $NHR_8$ in which $R_8$ represents a hydrogen atom or a $C_1$–$C_4$ alkyl radical,
$R_5$, which can be identical or different, represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue may be substituted,
$R_6$ and $R_7$, which may be identical or different, represent a hydrogen or halogen atom or a $C_1$–$C_4$ alkyl radical,
W represents a radical taken from the group comprising the following radicals:
—$(CH_2)_n$—; —$(CH_2)_m$—O—$(CH_2)_m$; —$(CH_2)_m$—CHOH—$(CH_2)_m$— and

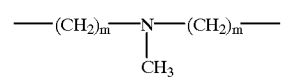

in which n is an integer ranging from 0 to 8 and m is an integer ranging from 0 to 4 inclusive.

Among the bis(phenyl)alkylenediamines of formula (IV) above, mention may be made more particularly of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)-ethylenediamine, N,N'-bis(4-aminophenyl) tetra-methylenediamine, N,N'-bis(β-hydroxyethyl)-N,N'-bis(4-aminophenyl)tetra-methylenediamine, N,N'-bis(4-methylaminophenyl)tetramethylenediamine and N,N'-bis(ethyl)-N,N'-bis(4'-amino-3'-methylphenyl)ethylenediamine and the addition salts thereof with an acid.

Among these bis(phenyl)alkylenediamines of formula (IV), N,N'-bis(β-hydroxyethyl)-N,N'-bis(4'-aminophenyl)-1,3-diamino-2-propanol or one of the addition salts thereof with an acid is particularly preferred.

the para-aminophenols corresponding to formula (V) below, and the addition salts thereof with an acid:

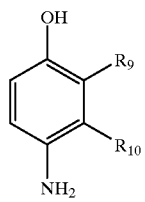

(V)

in which:

R$_9$ represents a hydrogen atom or a C$_1$–C$_4$ alkyl, C$_1$–C$_4$ monohydroxyalkyl, (C$_1$–C$_4$)alkoxy(C$_1$–C$_4$)alkyl, C$_1$–C$_4$ aminoalkyl or hydroxy(C$_1$–C$_4$)alkylamino (C$_1$–C$_4$)alkyl radical, R$_{10}$ represents a hydrogen or fluorine atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy(C$_1$–C$_4$)alkyl radical, it being understood that at least one of the radicals R$_9$ or R$_{10}$ represents a hydrogen atom.

Among the para-aminophenols of formula (V) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

the ortho-aminophenols which may be used as oxidation bases in the context of the present invention are chosen, in particular, from 2-aminophenol, 2-amino-1-hydroxy-5-methylbenzene, 2-amino-1-hydroxy-6-methylbenzene and 5-acetamido-2-aminophenol, and the addition salts thereof with an acid.

the heterocyclic bases which may be used as oxidation bases in the context of the present invention are chosen, in particular, from pyridine derivatives, pyrimidine derivatives and pyrazole derivatives, and the addition salts thereof with an acid.

Among the pyridine derivatives, mention may be made more particularly of the compounds described, for example, in GB patents 1,026,978 and 1,153,196, the disclosures of which are specifically incorporated herein by reference, such as 2,5-diaminopyridine, and the addition salts thereof with an acid.

Among the pyrimidine derivatives, mention may be made more particularly of the compounds described, for example, in German patents DE-2,359,399 or Japanese patents JP-88-169,571 and JP-91-333,495, the disclosures of which are specifically incorporated herein by reference, such as 2,4,5,6-tetraaminopyrimidine and 4-hydroxy-2,5,6-triaminopyrimidine, and the addition salts thereof with an acid.

Among the pyrazole derivatives, mention may be made more particularly of the compounds described in patents DE-3,843,892 and DE-4,133,957 and patent applications WO-94/08969 and WO-94/08970, the disclosures of which are specifically incorporated herein by reference, such as 4,5-diamino-1-methylpyrazole, 3,4-diaminopyrazole and 4,5-diamino-1-(4'-chlorobenzyl)pyrazole, and the addition salts thereof with an acid.

According to the invention, the oxidation base(s) preferably represent(s) from 0.0005 to 12% by weight approximately relative to the total weight of the composition (A) and even more preferably from 0.005 to 6% by weight approximately.

The couplers which may be used in the dyeing process according to the invention are those used conventionally in oxidation dye compositions, that is to say meta-phenylenediamines, meta-aminophenols and meta-diphenols, mono- or polyhydroxylated naphthalene derivatives, sesamol and its derivatives and heterocyclic compounds such as, for example, indole couplers, indolene couplers and pyridine couplers, and the addition salts thereof with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino4-(β-hydroxyethylamino)-1-methoxybenzene, 1,3-diaminobenzene, 1,3-bis(2,4-diaminophenoxy)-propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one and 1-phenyl-3-methylpyrazol-5-one and the addition salts thereof with an acid.

When they are present, these couplers preferably represent from 0.0001 to 10% by weight approximately relative to the total weight of the composition (A) and even more preferably from 0.005 to 5% by weight approximately.

In general, the addition salts with an acid of the oxidation bases and couplers are chosen in particular from the hydrochlorides, hydrobromides, sulphates, tartrates, lactates and acetates.

The composition (A) may also contain, in addition to the oxidation dye precursors defined above and any couplers which may be combined therewith, direct dyes in order to enrich the shades with glints. These direct dyes may preferably be chosen in particular from nitro dyes, azo dyes and anthraquinone dyes.

The composition (A) and/or the composition (B) may also more particularly contain at least one cationic or amphoteric substantive polymer as defined on pages 3 and 4 of patent application EP-0,673,641 A1, the disclosure of which is specifically incorporated herein by reference, and of which it is advantageously preferred to use:

the quaternary polyammonium polymers prepared and described in French patent 2,270,846, the disclosure of which is specifically incorporated herein by reference, comprising repeating units corresponding to formula (VI) below:

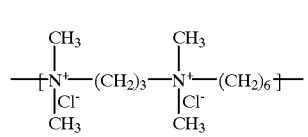

(VI)

and whose molecular weight, determined by gel permeation chromatography, ranges from 9500 to 9900;

the quaternary polyammonium polymers prepared and described in French patent 2,270,846, the disclosure of which is specifically incorporated herein by reference, comprising repeating units corresponding to formula (VII) below:

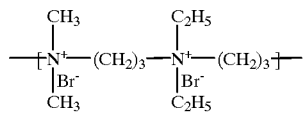

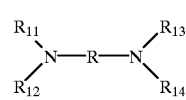

and whose molecular weight, determined by gel permeation chromatography, is about 1200.

The medium of composition (A) which is suitable for dyeing is preferably an aqueous medium comprising water and may optionally contain cosmetically acceptable organic solvents including, more particularly, alcohols such as ethyl alcohol, isopropyl alcohol, benzyl alcohol and phenylethyl alcohol, or glycols or glycol ethers such as, for example, ethylene glycol monomethyl, monoethyl and monobutyl ethers, propylene glycol or ethers thereof such as, for example, propylene glycol monomethyl ether, butylene glycol, dipropylene glycol and alkyl ethers of diethylene glycol such as, for example, diethylene glycol monoethyl ether or monobutyl ether, in concentrations ranging from about 0.5 to 20% and preferably from about 2 to 10% by weight relative to the total weight of the composition.

The composition (A) may also contain an effective amount of other agents, which are moreover previously known in oxidation dyeing, such as various common adjuvants, for instance sequestering agents, hair conditioners and in particular silicones, preserving agents, opacifiers, etc. and optionally anionic, nonionic or amphoteric surfactants or mixtures thereof.

The said composition may also contain antioxidants. These may be chosen in particular from sodium sulphite, thioglycolic acid, thiolactic acid, sodium bisulphite, dehydroascorbic acid, hydroquinone, 2-methylhydroquinone, tert-butylhydroquinone and homogenticic acid, and they are then generally present in amounts ranging from about 0.05 to 1.5% by weight relative to the total weight of the composition.

Obviously, a person skilled in the art will take care to choose the optional additional compound(s) mentioned above such that the advantageous properties intrinsically associated with the dye composition according to the invention are not, or are not substantially, adversely affected by the addition(s) envisaged.

In the composition (B), the oxidizing agent is preferably chosen from urea peroxide, alkali metal bromates or ferricyanides, and persalts such as perborates, percarbonates and persulphates. The use of hydrogen peroxide is particularly preferred.

The composition (B) advantageously comprises an aqueous hydrogen peroxide solution whose titre may range more particularly from about 2.5 to 40 volumes and even more preferably from about 5 to 20.

The pH of the ready-to-use composition applied to the keratin fibres (composition resulting from mixing the dye composition (A) and the oxidizing composition (B)) ranges generally from 4 to 11. It ranges more preferably from 6 to 10, and may be adjusted to the desired value by means of acidifying or basifying agents that are well known in the state of the art for dyeing keratin fibres.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (VIII) below:

in which R is a propylene residue optionally substituted with a hydroxyl group or a $C_1$–$C_4$ alkyl radical; $R_{11}$, $R_{12}$, $R_{13}$ and $R_{14}$, which may be identical or different, represent a hydrogen atom or a $C_1$–$C_4$ alkyl or $C_1$–$C_4$ hydroxyalkyl radical.

The acidifying agents are conventionally, by way of example, inorganic or organic acids such as hydrochloric acid, orthophosphoric acid, carboxylic acids such as tartaric acid, citric acid or lactic acid, or sulphonic acids.

The dyeing process according to the invention preferably comprises the steps of applying a mixture, prepared extemporaneously at the time of use from the compositions (A) and (B) described above, onto the dry or wet keratin fibres, and of leaving the mixture to act for an exposure time preferably ranging from 1 to 60 minutes approximately, and more preferably from 10 to 45 minutes approximately, in rinsing the fibres and then optionally in washing them with shampoo, then in rinsing them again and drying them.

Concrete examples illustrating the invention will now be given without, however, being limiting in nature.

EXAMPLE 1

The dye composition below, in accordance with the invention, was prepared:

Acrylic acid/$C_{10}$–$C_{30}$ alkyl acrylate crosslinked anionic amphiphilic polymer (Pemulen TR1 from Goodrich) . . . 1.0 g Oleic acid . . . 3.0 g Aqueous sodium bisulphite solution containing 35% AM* . . . 0.45 g AM*

Para-phenylenediamine . . . 0.162 g

Resorcinol . . . 0.165 g

Aqueous ammonia (20% $NH_3$) . . . 11.5 g

Sequestering agent . . . qs

Water . . . qs 100 g

AM*=active material

At the time of use, this composition was mixed, weight for weight, with a 20-volumes aqueous hydrogen peroxide solution and the mixture obtained was then applied to locks of natural hair containing 90% white hairs. After leaving the mixture on the locks for 10 minutes, they were rinsed and were then washed with a shampoo, rinsed again and then dried.

The chromaticity c* of the shade was measured, using an I.C.S. spectrocolorimeter, from the values of a* and b* in the L*, a*, b* international colour notation system from C.I.E.

The result was as follows: c*=14.36.

The value L* of the shade was also measured.

The result was as follows: L*=48.09.

COMPARATIVE EXAMPLE 2

Example 1 was repeated, replacing 1 gram of acrylic acid/$C_{10}$–$C_{30}$ alkyl acrylate crosslinked anionic amphiphilic polymer (Pemulen TR1 from Goodrich) by the mixture of the following two nonionic surfactants (allowing the same viscosity to be obtained): 18 grams of decyl alcohol ($C_{10}$–$C_{12}$–$C_{14}$/85-8.5–6.5) oxyethylenated with 3.5 mol of ethylene oxide, sold under the name Mergital BL 309 by the company Henkel, and 12 grams of decyl alcohol ($C_{10}$–$C_{12}$–$C_{14}$/85-8.5–6.5) oxyethylenated with 5.5 mol of ethylene oxide, sold under the name Mergital BL 589 by the company Henkel.

The same procedure as in Example 1 was then followed.

The results were as follows: c*=12.86

L*=49.72

CONCLUSION

The shade obtained according to the invention is more luminous (larger c*) than that obtained according to the prior art; it is also more intense (smaller L*).

We claim:

1. An oxidation dye composition for dyeing keratin fibres comprising at least one oxidation dye precursor, at least one anionic amphiphilic polymer containing at least one hydrophilic unit which is an unsaturated olefinic carboxylic acid, and at least one hydrophobic unit which is a ($C_{10}$–$C_{30}$) alkyl ester of unsaturated carboxylic acid.

2. A composition according to claim 1 wherein said keratin fibres are human keratin fibres.

3. A composition according to claim 2 wherein said human keratin fibres are hair.

4. A composition according to claim 1 wherein said composition further comprises a medium which is suitable for dyeing.

5. A composition according to claim 1 wherein said at least one hydrophilic unit is a monomer of the formula (I):

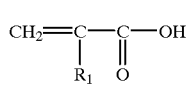

(I)

wherein $R_1$ denotes H, $CH_3$ or $C_2H_5$.

6. A composition according to claim 5 wherein said monomer is selected from acrylic acid and methacrylic acid.

7. A composition according to claim 1 wherein said at least one hydrophobic unit is a monomer of the formula (II):

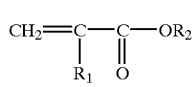

(II)

wherein $R_1$ denotes H, $CH_3$ or $C_2H_5$, and $R_2$ denotes a $C_{10}$–$C_{30}$ alkyl radical.

8. A composition according to claim 7 wherein $R_1$ denotes H or $CH_3$.

9. A composition according to claim 7 wherein $R_2$ denotes a $C_{12}$–$C_{22}$ alkyl radical.

10. A composition according to claim 1 wherein said at least one anionic amphiphilic polymer is crosslinked.

11. A composition according to claim 1 wherein said at least one anionic amphiphilic polymer is a polymer formed from a mixture of monomers comprising acrylic acid, an ester of formula (II) below:

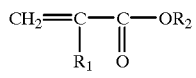

(II)

wherein $R_1$ denotes H or $CH_3$ and $R_2$ denotes an alkyl radical having from 12 to 22 carbon atoms, and a crosslinking agent.

12. A composition according to claim 1 wherein said at least one anionic amphiphilic polymer is a polymer of acrylic acid and of lauryl methacrylate.

13. A composition according to claim 1 wherein said at least one oxidation dye precursor is selected from ortho- and para-phenylenediamines, bis(phenyl)alkylenediamines, ortho- and para-aminophenols, heterocyclic bases, and acid addition salts thereof.

14. A composition according to claim 1 wherein said at least one oxidation dye precursor is present in concentrations ranging from 0.0005 to 12% by weight approximately relative to the total weight of the composition.

15. A composition according to claim 1, further comprising at least one coupler.

16. A composition according to claim 15 wherein said at least one coupler is selected from meta-phenylenediamines, meta-aminophenols, meta-diphenols, heterocyclic couplers, and acid addition salts thereof.

17. A composition according to claim 15 wherein said at least one coupler ranges from 0.0001% to 10% by weight approximately relative to the total weight of the composition.

18. A composition according to claim 13 wherein said acid addition salts are selected from hydrochlorides, hydrobromides, sulphates, tartrates, lactates and acetates.

19. A composition according to claim 16 wherein said acid addition salts are selected from hydrochlorides, hydrobromides, sulphates, tartrates, lactates and acetates.

20. A composition according to claim 1 wherein said composition further comprises at least one direct dye.

21. A composition according to claim 1 wherein said composition further comprises at least one substantive polymer selected from cationic and amphoteric substantive polymers.

22. A composition according to claim 21 wherein said at least one substantive polymer is selected from quaternary polyammonium polymers comprising repeating units of formula (VI) below:

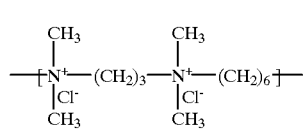

(VI)

23. A composition according to claim 21 wherein said at least one substantive polymer is selected from quaternary polyammonium polymers comprising repeating units of formula (VII) below:

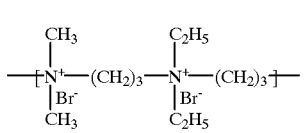

(VII)

24. A composition according to claim 1 wherein said composition further comprises at least one reducing agent present in amounts ranging from 0.05 to 3% by weight relative to the total weight of the composition.

25. A ready-to-use composition according to claim 1 wherein said composition further comprises an oxidizing agent.

26. A composition according to claim 25 wherein said composition has a pH ranging from 4 to 11.

27. A composition according to claim 25 wherein said oxidizing agent is selected from hydrogen peroxide, urea peroxide, alkali metal bromates, ferricyanides, and persalts.

28. A composition according to claim 25 wherein said oxidizing agent is an aqueous hydrogen peroxide solution whose titre ranges from 2.5 to 40 volumes.

29. A composition according to claim 1 wherein said at least one anionic amphiphilic polymer is present in an amount ranging from 0.05 to 10% by weight relative to the total weight of the composition applied to the fibres.

30. A composition according to claim 29 wherein said at least one anionic amphiphilic polymer is present in an amount ranging from 0.2 to 5% by weight relative to the total weight of the composition applied to the fibres.

31. A process for dyeing keratin fibres comprising the steps of applying to said fibres a dye composition according to claim 1, and of developing the colour in alkaline, neutral or acidic medium by the addition of an oxidizing agent.

32. A process according to claim 31 wherein said keratin fibres are human keratin fibres.

33. A process according to claim 32 wherein said human keratin fibres are hair.

34. A process according to claim 31 wherein said oxidizing agent is combined with said dye composition and thereafter said dye composition and said oxidizing agent are applied to said fibres.

35. A process according to claim 31 wherein said dye composition is applied to said fibres and thereafter said oxidizing agent is applied to said fibres.

36. A process according to claim 31 wherein said oxidizing agent is applied to said fibres and thereafter said dye composition is applied to said fibres.

37. A process according to claim 31 wherein said oxidizing agent and said dye composition are separately and simultaneously applied to said fibres.

38. A process according to claim 31 wherein said oxidizing agent is present in an oxidizing composition that is applied to said fibres and thereafter said dye composition is applied without intermediate rinsing to said fibres.

39. A process according to claim 31 wherein said oxidizing agent is present in an oxidizing composition that is applied without intermediate rinsing to said fibres after said dye composition is applied to said fibres.

40. A multi-compartment device or kit for dyeing keratin fibres comprising at least two compartments, one containing a composition according to claim 1, and another containing a composition comprising an oxidizing agent in a medium which is suitable for dyeing.

41. A multi-compartment device or kit according to claim 40 wherein said keratin fibres are human keratin fibres.

42. A multi-compartment device or kit according to claim 41 wherein said human keratin fibres are hair.

43. A process for the oxidation dyeing of human keratin fibres comprising the step of applying to said fibres at least one oxidation dye composition according to claim 1.

44. A process according to claim 43 wherein said human keratin fibres are hair.

45. A process for the oxidation dyeing of human keratin fibres comprising the step of applying to said fibres the contents of said multi-compartment kit or device according to claim 40.

46. A process according to claim 45 wherein said human keratin fibres are hair.

47. A process for dyeing keratin fibres comprising the steps of applying to said fibres a dye composition comprising, in a medium which is suitable for dyeing, at least one oxidation dye precursor, and of developing the colour in alkaline, neutral or acidic medium by the addition of an oxidizing composition comprising an oxidizing agent and an effective amount of at least one anionic amphiphilic polymer containing at least one hydrophilic unit which is an unsaturated olefinic carboxylic acid and at least one hydrophobic unit which is a ($C_{10}$–$C_{30}$) alkyl ester of unsaturated carboxylic acid.

48. A process according to claim 47 wherein said keratin fibres are human keratin fibres.

49. A process according to claim 48 wherein said human keratin fibres are hair.

50. A process according to claim 47 wherein said oxidizing composition is combined with said dye composition and thereafter said dye composition and said oxidizing composition are applied to said fibres.

51. A process according to claim 47 wherein said dye composition is applied to said fibres and thereafter said oxidizing composition is applied without intermediate rinsing to said fibres.

52. A process according to claim 47 wherein said oxidizing composition is applied to said fibres and thereafter said dye composition is applied without intermediate rinsing to said fibres.

53. A process according to claim 47 wherein said oxidizing composition and said dye composition are separately and simultaneously applied to said fibres.

54. A multi-compartment device or kit for dyeing keratin fibres comprising at least two compartments, one containing a dye composition according to claim 47, and another containing an oxidizing composition according to claim 47.

55. A multi-compartment device or kit according to claim 54 wherein said keratin fibres are human keratin fibres.

56. A multi-compartment device or kit according to claim 55 wherein said human keratin fibres are hair.

57. A process for the oxidation dyeing of human keratin fibres comprising the step of applying to said fibres the contents of said multi-compartment kit or device according to claim 54.

58. A process according to claim 57 wherein said human keratin fibres are hair.

59. A process according to claim 47, wherein said dye composition further comprises at least one coupler, and at least one anionic amphiphilic polymer containing at least one hydrophilic unit which is an unsaturated olefinic carboxylic acid and at least one hydrophobic unit which is a ($C_{10}$–$C_{30}$) alkyl ester of unsaturated carboxylic acid.

* * * * *